United States Patent [19]

Schumacher et al.

[11] Patent Number: 4,589,908
[45] Date of Patent: May 20, 1986

[54] HERBICIDAL AGENTS

[75] Inventors: Hans Schumacher, Flörsheim am Main; Rudolf Heinrich, Kelkheim; Hans-Günter Marks, Hattersheim am Main, all of Fed. Rep. of Germany

[73] Assignee: Hoechst Aktiengesellschaft, Frankfurt, Fed. Rep. of Germany

[21] Appl. No.: 734,756

[22] Filed: May 15, 1985

Related U.S. Application Data

[63] Continuation of Ser. No. 547,737, Nov. 1, 1983.

[30] Foreign Application Priority Data

Nov. 4, 1982 [DE] Fed. Rep. of Germany ....... 3240694

[51] Int. Cl.$^4$ ...................... A01N 43/76; A01N 37/40
[52] U.S. Cl. ........................................... 71/88; 71/108
[58] Field of Search ..................... 71/88, 108

[56] References Cited

U.S. PATENT DOCUMENTS

| | | | |
|---|---|---|---|
| 3,954,442 | 5/1976 | Becker et al. | 71/108 |
| 4,336,057 | 6/1982 | Bieringer et al. | 71/88 |
| 4,370,489 | 1/1983 | Boesenberg et al. | 71/108 |
| 4,383,850 | 5/1983 | Handte et al. | 71/88 |
| 4,401,459 | 8/1983 | Satomi et al. | 71/108 |

FOREIGN PATENT DOCUMENTS

| | | | |
|---|---|---|---|
| 2745482 | 4/1979 | Fed. Rep. of Germany | 71/88 |
| 2745869 | 4/1979 | Fed. Rep. of Germany | 71/88 |
| 3006439 | 8/1981 | Fed. Rep. of Germany | 71/88 |

Primary Examiner—Glennon H. Hollrah
Assistant Examiner—Andrew Duff Meikle
Attorney, Agent, or Firm—Curtis, Morris & Safford

[57] ABSTRACT

Combinations of herbicides of the formula (I)

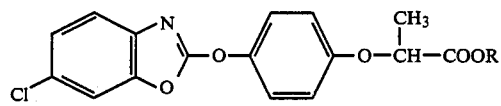

(I)

wherein R denotes H, alkyl or one cation equivalent, with herbicides of the formula (II)

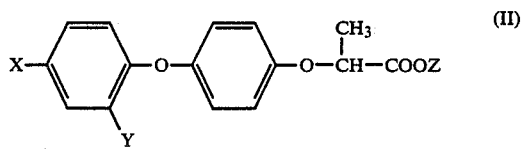

(II)

wherein X denotes Cl or Br, Y denotes H or Cl and Z denotes alkyl, and if X is Br, Y must be Cl, possess surprising synergistic properties in controlling weeds.

2 Claims, No Drawings

HERBICIDAL AGENTS

This is a continuation of application Ser. No. 547,737, filed Nov. 1, 1983.

The present invention relates to herbicidal agents which contain a compound of the formula (I)

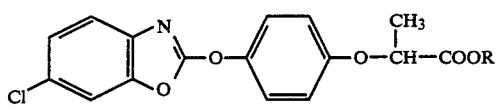

wherein R is H, $(C_1-C_4)$-alkyl or one cation equivalent of a base,
in combination with a compound of the formula (II)

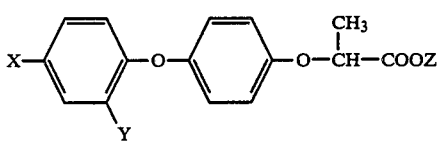

wherein
X is Cl or Br,
Y is H or Cl and
Z is $(C_1-C_4)$-alkyl,
and if X is Br, Y must be Cl.

Preferred compounds of the formula I are those in which R is $C_2H_5$; preferred compounds of the formula II are those in which X and Y are Cl and Z is $CH_3$.

The compounds of the formula I are described in German Offenlegungsschrift No. 2,640,730, and the compounds of the formula II are described in German Offenlegungsschrift No. 2,223,894.

The compounds of the formulae I and II possess an asymmetric carbon center and can therefore occur as pure stereoisomers (enantiomers) or as mixtures of enantiomers.

Suitable cation equivalents of the radicals R of the formula I are, in particular, alkali metal cations, such as $Na^+$ or $K^+$, alkaline earth metal cations, such as $Mg^{2+}$ or $Ca^{2+}$, or unsubstituted or substituted ammonium ions.

The compounds of the two formulae I and II are suitable for controlling grasses in dicotyledonous crops (for example beans, sugar beet and rape) and in cereal crops.

The compounds of the formula I are particularly highly active against Panicum-like grasses, for example Setaria sp., Echinochloa sp., Sorghum sp. and others; on the other hand, perennial rye grasses (Lolium sp.) are not damaged.

In addition to the action against Panicum-like grasses, compounds of the formula II exhibit high activity against Lolium sp. and against wild oats (Avena sp.).

In experiments to combine the two active compounds to extend the action spectrum, a striking synergistic effect was surprisingly found.

The active compound combinations according to the invention can be employed for controlling undesirable grasses, such as, for example, Avena sp., Setaria sp., Alopecurus myosuroides, Brachiaria sp., Digitaria sp., Echinochloa sp., Eleusine indica, Lolium sp., Panicum sp., Zea mais and Sorghum sp., and in crops, such as, wheat, beets, rape, flax, sunflowers, onions, potatoes, beans, peas, lucerne and other leguminosae.

The weight ratios of components I and II in the combinations according to the invention can vary within wide limits, it being possible for the ratio I:II to vary in the range from 15:1 to 1:15; it is, in particular, in the range from 5:1 to 1:10, particularly preferably in the range from 1:2 to 1:10.

The combinations according to the invention can be used either as tank mixtures, in which the individual active compounds are mixed together only directly before application, or as ready-to-use formulations. As ready-to-use mixtures, they can be formulated, for example, in the form of wettable powders, emulsifiable concentrates, solutions, dispersions, dusting agents or granules, and contain, if appropriate, the conventional formulation auxiliaries, such as wetting agents, adhesives, emulsifiers, dispersants, inert solid or liquid substances, milling assistants and solvents.

Wettable powders are preparations which can be dispersed homogeneously in water and which, in addition to the active compound and if appropriate diluents or inert substances, can also contain wetting agents, for example polyoxyethylated alkylphenols, polyoxyethylated oleylamines or stearylamines, alkylsulfonates or alkylphenylsulfonates, and dispersants, for example sodium ligninsulfonate, sodium 2,2'-dinaphthylmethane-6,6'-disulfonate, sodium dibutylnaphthalenesulfonate or sodium oleylmethyltaurate.

Emulsifiable concentrates can be prepared, for example, by dissolving the active compound in an organic solvent, for example butanol, cyclohexanone, dimethylformamide, xylene, isophorone or relatively high boiling aromatics, with the addition of one or more emulsifiers. The following can, for example, be used as emulsifiers: calcium alkylarylsulfonates, fatty acid polyglycol esters, alkylaryl polyglycol ethers, fatty alcohol polyglycol ethers, polyoxyethylated oleylamines or stearylamines, propylene oxide/ethylene oxide condensation products, alkylpolyethers, sorbitane fatty acid esters, alkylarylpropylene oxide/ethylene oxide condensation products, etc.

Dusting agents are obtained by milling the active compound with finely divided, solid substances, for example talc, natural clays, such as kaolin, bentonite or pyrophillite, or diatomaceous earth.

Granules can be prepared either by spraying a solution of the active compound onto adsorptive, granulated inert material, or by applying active compound concentrates by means of a binder, for example polyvinyl alcohol, sodium polyacrylate, methylhydroxyethylcellulose or mineral oils, onto the surface of carriers, such as sand or kaolinites, or of granulated inert material. Suitable active compound formulations can also be prepared in the manner conventionally used for the preparation of fertilizer granules—if desired, as a mixture with fertilizers.

The synergistic active compound mixtures according to the invention, comprising compounds of the formulae I and II, can be formulated in the form of conventional preparations, in particular as wettable powders, emulsifiable concentrates, solutions, dispersions, dusting agents or granules. The total active compound content of the marketable formulations is then about 2 to 95% by weight, preferably 10 to 70% by weight, the remainder up to 100% by weight consisting of conventional formulation auxiliaries, such as adhesives, wetting agents, emulsifiers, dispersants, fillers, solvents and carriers.

In wettable powders, the total active compound concentration varies in a range from about 10 to 70% by weight, and the concentrations of the individual components I and II can be between 3 and 50% by weight, depending on the ratio of the components I and II. The remainder up to 100% by weight consists of conventional formulation auxiliaries. In the case of emulsifiable concentrates, the total active compound concentration is in a range from about 10 to 70% by weight, and the concentration of component I can vary between 3 and 30% by weight and the concentration of component II can vary between 3 and 40% by weight, depending on the ratio of components I and II. In the case of granules, it is about 2 to 10% by weight. Dust-like formulations contain about 5 to 20% by weight of active compound mixture.

The present invention therefore also relates to herbicidal agents which contain from 2 to 95% by weight, preferably from 10 to 70% by weight, of an active compound combination of compounds of the formulae I and II, the remainder up to 100% by weight consisting of conventional formulation auxiliaries.

For use, the stated concentrates are, if appropriate, diluted in a conventional manner, for example wettable powders, emulsifiable concentrates and dispersions by means of water. Dust-like and granulated preparations and sprayable solutions are not generally diluted with further inert substances before use. The required application rate of the agents according to the invention also varies with the external conditions, such as temperature, moisture, etc. It can vary within wide limits, and is in general between 0.2 and 10 kg/ha of active compound combination, preferably 0.3–1.5 kg/ha.

The examples which follow illustrate the invention.

A. Formulation Examples

EXAMPLES 1–6: PREPARATION OF EMULSIFIABLE CONCENTRATES

General Method:

Component I is dissolved in the appropriate solvent mixture at 60°–70° C., and the molten component II is then added. The individual emulsifier components are added while stirring thoroughly, and the mixture is allowed to cool. The emulsifiable concentrates have a slight to moderate brown coloration.

Using this procedure, the components stated in Examples 1–6 of the table below, and formulation auxiliaries, are mixed together. The numerical values in the table correspond to parts by weight.

|  | Example 1–6: | | | | | |
|---|---|---|---|---|---|---|
|  | (1) | (2) | (3) | (4) | (5) | (6) |
| Ratio: I to II | 1:1 | 1:2 | 1:5 | 1:10 | 2:1 | 5:1 |
| Component I | 120 | 100 | 50 | 25 | 160 | 200 |
| Component II | 120 | 200 | 250 | 250 | 80 | 40 |
| Xylene | 420 | 500 | 500 | 500 | 400 | 300 |
| Isophorone | 200 | 110 | — | 100 | — | — |
| Cyclohexanone | — | — | 100 | — | — | — |
| Dimethylformamide | — | — | — | — | 200 | 350 |
| Calcium dodecylbenzene-sulfonate | 40 | 50 | 50 | 40 | 60 | 40 |
| Ethoxylated castor oil (40 units of ethylene oxide) | 70 | — | — | 60 | 50 | 40 |
| Ethoxylated nonylphenol (10 units of ethylene oxide) | — | 40 | — | — | — | — |
| Ethoxylated tributylphenol (12 units of ethylene oxide) | — | — | 50 | — | — | 30 |
| Ethoxylated oleyl alcohol (15 units of ethylene oxide) | 30 | — | — | 25 | 50 | — |

EXAMPLES 7 AND 8: PREPARATION OF WETTABLE POWDERS

EXAMPLE 7

Component I and component II (1:2)

A readily water-dispersible wettable powdeer is obtained by a method in which 100 parts by weight of component I
200 parts by weight of component II
500 parts by weight of basic aluminum silicate (kaolinite)
80 parts by weight of potassium ligninsulfonate
40 parts by weight of sodium oleylmethyltaurate are thoroughly mixed in a drum mixer and then comminuted once on a pinned-disc mill at 3,000 rpm. The resulting mill base is again mixed, and is milled once at 12,000 rpm.

EXAMPLE 8

Component I and component II (1:5)

A readily water-dispersible wettable powder is obtained from:

50 parts by weight of component I
250 parts by weight of component II
350 parts by weight of synthetic silica
80 parts by weight of potassium ligninsulfonate
50 parts by weight of polyarylsulfonate (Na salt)
50 parts by weight of sodium oleylmethyltaurate
40 parts by weight of polyvinyl alcohol
130 parts by weight of basic aluminum silicate.

The molten active compound (component II) is adsorbed onto the synthetic silica in a drum mixer and then mixed thoroughly with the remaining formulation components, and the mixture is milled on a pinned-disc mill once at 3,000 rpm and then once at 12,000 rpm.

B. Biological Examples

In the biological examples below, in order to assess the synergistic effect, a distinction is made between the additive efficiency calculated from the actions achieved when the active compound components are used individually, and the experimentally found efficiency of the active compound combinations.

The additive efficiency is calculated according to the formula of S. R. Colby (cf. Calculating Synergistic and Antagonistic Responses of Herbicide Combinations in Weeds, 15, 1967, pages 20–22).

This formula is as follows:

$$E = X + Y - X \cdot Y/100$$

wherein

X denotes % damage by herbicide I at an application rate of X kg/ha,

Y denotes % damage by herbicide II at an application rate of Y kg/ha and

E denotes the expected damage by herbicides I and II at an application rate of X+Y kg/ha.

If the actual damage is greater than the calculated one, the action of the combination is more than additive, i.e. a synergistic effect is present.

The biological results were obtained using the weeds *Avena fatua, Lolium multiflorum, Alopecurus myosuroides* and *Setaria lutescens* and the crop plants *Vicia faba* and *Triticum aestivum*.

The plants were grown in a greenhouse, in Neubauer dishes filled with soil, and were sprayed, in the 3-4 leaf stage, with the individual active compounds and with the active compound combinations according to the invention, in 300 liters of water per ha. They were rated 4 weeks later, and the damage (action) was expressed as a percentage compared with the untreated control.

The results are reproduced in Tables I-III below, the values to be expected from the formula due to Colby being given in ().

As shown by the biological results of Tables I-III, the herbicidal actions calculated according to Colby are substantially exceeded by those of the combinations according to the invention, while the crop plants are not damaged.

TABLE I

| Compound of formula I | Active compound dose g/ha | Damage in % (action) | | | |
|---|---|---|---|---|---|
| | | Avena fatua | Lolium multiflorum | Alopecurus myosuroides | Setaria lutescens |
| A | 10 | 0 | 6 | 7 | 15 |
| | 15 | 6 | 9 | 7 | 44 |
| | 20 | 9 | 9 | 10 | 63 |
| | 30 | 19 | 12 | 13 | 67 |
| | 50 | 32 | 13 | 15 | 89 |
| | 60 | 38 | 22 | 20 | 93 |
| | 75 | 52 | 26 | 21 | 93 |
| | 100 | 60 | 26 | 27 | 93 |
| | 120 | 67 | 27 | 31 | 96 |
| | 150 | 70 | 27 | 37 | 98 |

A = Ethyl 2-[4-(6-chloro-benzoxazol-2-yloxy)-phenoxy]-propionate

TABLE II

| Compound of formula I | Active compound dose g/ha | Damage in % (action) | | | |
|---|---|---|---|---|---|
| | | Avena fatua | Lolium multiflorum | Alopecurus myosuroides | Setaria lutescens |
| B | 10 | 0 | 21 | 2 | 7 |
| | 15 | 0 | 23 | 7 | 9 |
| | 20 | 0 | 27 | 8 | 13 |
| | 30 | 7 | 28 | 8 | 19 |
| | 50 | 7 | 50 | 8 | 53 |
| | 60 | 9 | 52 | 11 | 59 |
| | 100 | 9 | 64 | 15 | 66 |
| | 150 | 13 | 70 | 20 | 70 |

B = Methyl 2-[4-(2,4-dichlorophenoxy)-phenoxy]-propionate

TABLE III

| Compounds of formulae I and II | Active compound dose g/ha | Damage in % (action) | | | | | |
|---|---|---|---|---|---|---|---|
| | | Avena fatua | Lolium multiflorum | Alopecurus myosuroides | Setaria lutescens | Vicia faba | Triticum aestivum |
| A + B (weight ratio 1:1) | 20 + 20 | — | — | — | 87 (66) | 0 | 0 |
| | 30 + 30 | — | — | — | 91 (74) | 0 | 0 |
| | 50 + 50 | 68 (37) | 65 (57) | 62 (22) | — | 0 | 0 |
| | 100 + 100 | 76 (64) | 84 (74) | 68 (38) | — | 0 | 0 |
| | 150 + 150 | 95 (74) | 99 (79) | 83 (50) | — | 0 | 0 |
| A + B (weight ratio 1:2) | 15 + 30 | — | — | — | 91 (55) | 0 | 0 |
| | 30 + 60 | 63 (27) | 67 (58) | 51 (23) | 97 (77) | 0 | 0 |
| | 50 + 100 | 68 (39) | 79 (69) | 68 (28) | — | 0 | 0 |
| | 75 + 150 | 90 (59) | 96 (78) | 87 (37) | — | 0 | 0 |
| A + B (weight ratio 1:5) | 10 + 50 | — | — | — | 87 (61) | 0 | 0 |
| | 20 + 100 | 52 (20) | 75 (68) | 61 (24) | 92 (88) | 0 | 0 |
| | 30 + 150 | 62 (30) | 86 (74) | 73 (31) | — | 0 | 0 |
| A + B (weight ratio 1:10) | 10 + 100 | — | — | — | 84 (72) | 0 | 0 |
| | 15 + 150 | 65 (19) | 80 (73) | 67 (26) | 97 (26) | 0 | 0 |
| A + B (weight ratio 2:1) | 20 + 10 | — | — | — | 93 (66) | 0 | 0 |
| | 30 + 15 | — | — | — | 95 (70) | 0 | 0 |
| | 60 + 30 | 72 (43) | 53 (44) | 61 (27) | — | 0 | 0 |
| | 120 + 60 | 95 (70) | 86 (65) | 82 (39) | — | 0 | 5 |
| A + B (weight ratio 5:1) | 50 + 10 | — | — | — | 98 (90) | 0 | 0 |
| | 75 + 15 | — | — | — | 100 (94) | 0 | 0 |
| | 100 + 20 | 73 (60) | 55 (46) | 54 (33) | — | 0 | 3 |
| | 150 + 30 | 90 (73) | 76 (48) | 85 (43) | — | 0 | 6 |

We claim:

1. A herbicidal agent, which consists essentially of an effective amount of a mixture of a first compound of the formula

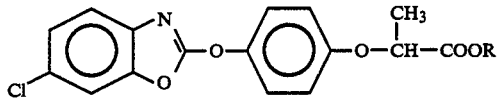

wherein R is ethyl, and a second compound of the formula

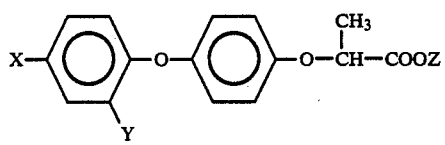

wherein X and Y are chlorine and Z is methyl, the ratio of the amounts of the respective compounds being in a range of from 5:1 to 1:10.

2. A herbicidal agent as claimed in claim 1 wherein the ratio of the first compound to the second compound is between 1:2 and 1:10.

* * * * *